United States Patent
Copland et al.

(10) Patent No.: US 9,706,912 B2
(45) Date of Patent: Jul. 18, 2017

(54) OPTICAL MEASUREMENT SYSTEM AND METHOD INCLUDING BLINK RATE MONITOR AND/OR TEAR FILM BREAKUP DETECTOR

(71) Applicant: AMO WAVEFRONT SCIENCES, LLC, Albuquerque, NM (US)

(72) Inventors: Richard J. Copland, Albuquerque, NM (US); John G. Dixson, Albuquerque, NM (US)

(73) Assignee: AMO WAVEFRONT SCIENCES, LLC, Santa Ana, CA (US)

( * ) Notice: Subject to any disclaimer, the term of this patent is extended or adjusted under 35 U.S.C. 154(b) by 60 days.

(21) Appl. No.: 14/789,943

(22) Filed: Jul. 1, 2015

(65) Prior Publication Data
US 2016/0000318 A1 Jan. 7, 2016

Related U.S. Application Data (60) Provisional application No. 62/020,268, filed on Jul. 2, 2014.

(51) Int. Cl.
*A61B 3/14* (2006.01)
*A61B 3/10* (2006.01)
(Continued)

(52) U.S. Cl.
CPC ............ *A61B 3/101* (2013.01); *A61B 3/0033* (2013.01); *A61B 3/113* (2013.01); *A61B 3/14* (2013.01); *A61B 3/152* (2013.01); *A61B 5/1103* (2013.01)

(58) Field of Classification Search
CPC ....... A61B 3/1005; A61B 3/101; A61B 3/102; A61B 3/10; A61B 3/14
(Continued)

(56) References Cited

U.S. PATENT DOCUMENTS

| 5,777,719 A | 7/1998 | Williams et al. |
| 6,550,917 B1 | 4/2003 | Neal et al. |

(Continued)

FOREIGN PATENT DOCUMENTS

| AU | 2008229893 A1 | 5/2009 |
| JP | 2000254099 A | 9/2000 |
| JP | 2004275697 A | 10/2004 |

OTHER PUBLICATIONS

International Search Report and Written Opinion for Application No. PCT/US2015/038915, mailed on Oct. 19, 2015, 10 pages.

(Continued)

*Primary Examiner* — Hung Dang
(74) *Attorney, Agent, or Firm* — Abbott Medical Optics Inc.

(57) ABSTRACT

An optical measurement system and method measure a characteristic of a subject's eye. The optical measurement system receives from an operator, via a user interface of the optical measurement instrument, a begin measurement instruction indicating the start of a measurement period for objectively measuring at least one characteristic of the subject's eye. Subsequent to receiving the begin measurement instruction, the optical measurement system determines whether a criterion associated with the tear film quality of the subject's eye is not satisfied. In response to determining that the criterion is not satisfied, the optical measurement instrument takes one or more corrective actions to measure the characteristic of the subject's eye under a condition wherein the criterion is satisfied.

26 Claims, 8 Drawing Sheets

(51) Int. Cl.
     *A61B 3/15*  (2006.01)
     *A61B 3/00*  (2006.01)
     *A61B 3/113* (2006.01)
     *A61B 5/11*  (2006.01)

(58) Field of Classification Search
     USPC ............... 351/205, 206, 208, 246, 200, 212
     See application file for complete search history.

(56) References Cited

U.S. PATENT DOCUMENTS

| | | |
|---|---|---|
| 7,976,163 B2 | 7/2011 | Campbell et al. |
| 2007/0171365 A1 | 7/2007 | Tuan |
| 2007/0229760 A1 | 10/2007 | Hirohara et al. |
| 2010/0253907 A1* | 10/2010 | Korb .................... A61B 3/0025 351/206 |
| 2012/0300174 A1 | 11/2012 | Yokoi et al. |

OTHER PUBLICATIONS

Singh M., et al., "Drowsy Detection on Eye Blink Duration Using Algorithm," International Journal of Emerging Technology and Advanced Engineering, 2012, vol. 2 (4), pp. 363-365.

* cited by examiner

OPTICAL MEASUREMENT SYSTEM AND METHOD INCLUDING BLINK RATE MONITOR AND/OR TEAR FILM BREAKUP DETECTOR

CROSS-REFERENCE TO RELATED APPLICATION

This application claims priority to U.S. Provisional Application No. 62/020,268 filed on Jul. 2, 2014, hereby incorporated by reference in its entirety.

FIELD OF INVENTION

Embodiments of this invention generally pertain to the field of vision diagnostics, and particularly to a method and system for objectively measuring an optical characteristic, such as the corneal topography, or refraction of an eye.

BACKGROUND

Ocular aberrations typically produce unwanted results in the form of bad eyesight. To be adequately treatable, these aberrations need to be measured and characterized. To this end, various devices, apparatuses, and methods have been developed for objectively measuring characteristics, including aberrations, of a subject's eye.

During vision measurements, however, sometimes a subject will stare into the optical measurement apparatus for an unusually long period of time without blinking. When this happens, some individuals will experience a disruption of the tear film on their eye(s). The tear film consists of three layers: (1) an outer lipid layer that inhibits evaporation; (2) an inner aqueous layer; and (3) a mucin layer that lies on the cornea. The cornea repels water, so it is the function of the mucin layer to coat the cornea, and to provide a hydrophilic layer for the aqueous layer to be spread over evenly. In particular, if a subject holds her/his eye open for too long without blinking, the mucin layer may become disrupted. If that happens, it may take several minutes for the mucin layer to recoat the entire cornea. Until that happens, measurements of the eye made during the intervening period will not reflect the eye's normal optical performance. More specifically, if the corneal topography and/or refraction of the eye are measured under such a condition when the tear film layer has been disrupted, the measurement will include errors.

SUMMARY OF THE INVENTION

Therefore, it would be desirable to provide an optical measurement system and method which can ensure that measurements are performed when the tear film is of an acceptable quality to permit measurements that accurately conform to the "real world" optical performance of the eye so as to obviate one or more problems due to limitations and disadvantages of the related art.

In one aspect of the invention, a method is provided for measuring a characteristic of a subject's eye. The method comprises: an optical measurement instrument receiving from an operator, via a user interface of the optical measurement instrument, a begin measurement instruction indicating the start of a measurement period for objectively measuring at least one characteristic of the subject's eye; subsequent to receiving the begin measurement instruction, determining whether a criterion associated with the tear film quality of the subject's eye is not satisfied; and in response to determining that the criterion is not satisfied, taking one or more corrective actions to measure the characteristic of the subject's eye under a condition wherein the criterion is satisfied.

In another aspect of the invention, an optical measurement instrument comprises: an optical system configured for objectively measuring at least one characteristic of a subject's eye; a user interface; and one or more processors. The one or more processors are configured to receive via the user interface a begin measurement instruction indicating the start of a measurement period for objectively measuring at least one characteristic of the subject's eye, subsequent to receiving the begin measurement instruction to determine whether a criterion associated with the tear film quality of the subject's eye is satisfied, and in response to determining that the criterion is not satisfied, to take one or more corrective actions to measure the characteristic of the subject's eye under a condition where the criterion is satisfied.

This summary and the following description are merely exemplary, illustrative, and explanatory, and are not intended to limit, but to provide further explanation of the invention as claimed. Additional features, aspects, objects and advantages of embodiments of this invention are set forth in the descriptions, drawings, and the claims, and in part, will be apparent from the drawings and detailed description, or may be learned by practice. The claims are incorporated by reference.

BRIEF DESCRIPTION OF THE DRAWINGS

The novel features of the invention are set forth with particularity in the appended claims. A better understanding of the features and advantages of the present invention will be obtained by referring to the following detailed description that sets forth illustrative embodiments using principles of the invention, as well as to the accompanying drawings of which:

DETAILED DESCRIPTION

As discussed above, it would be desirable to provide an optical measurement system and method of operation of an optical measurement system which can insure that the tear film quality of a subject's eye satisfies some specified criterion or criteria when measuring one or more characteristics of the eye. The following description describes various embodiments of the present invention. For purposes of explanation, specific configurations and details are set forth so as to provide a thorough understanding of the embodiments. It will also, however, be apparent to one skilled in the art that embodiments of the present invention can be practiced without certain specific details. Further, to avoid obscuring the embodiment being described, various well-known features may be omitted or simplified in the description.

Figure 1:
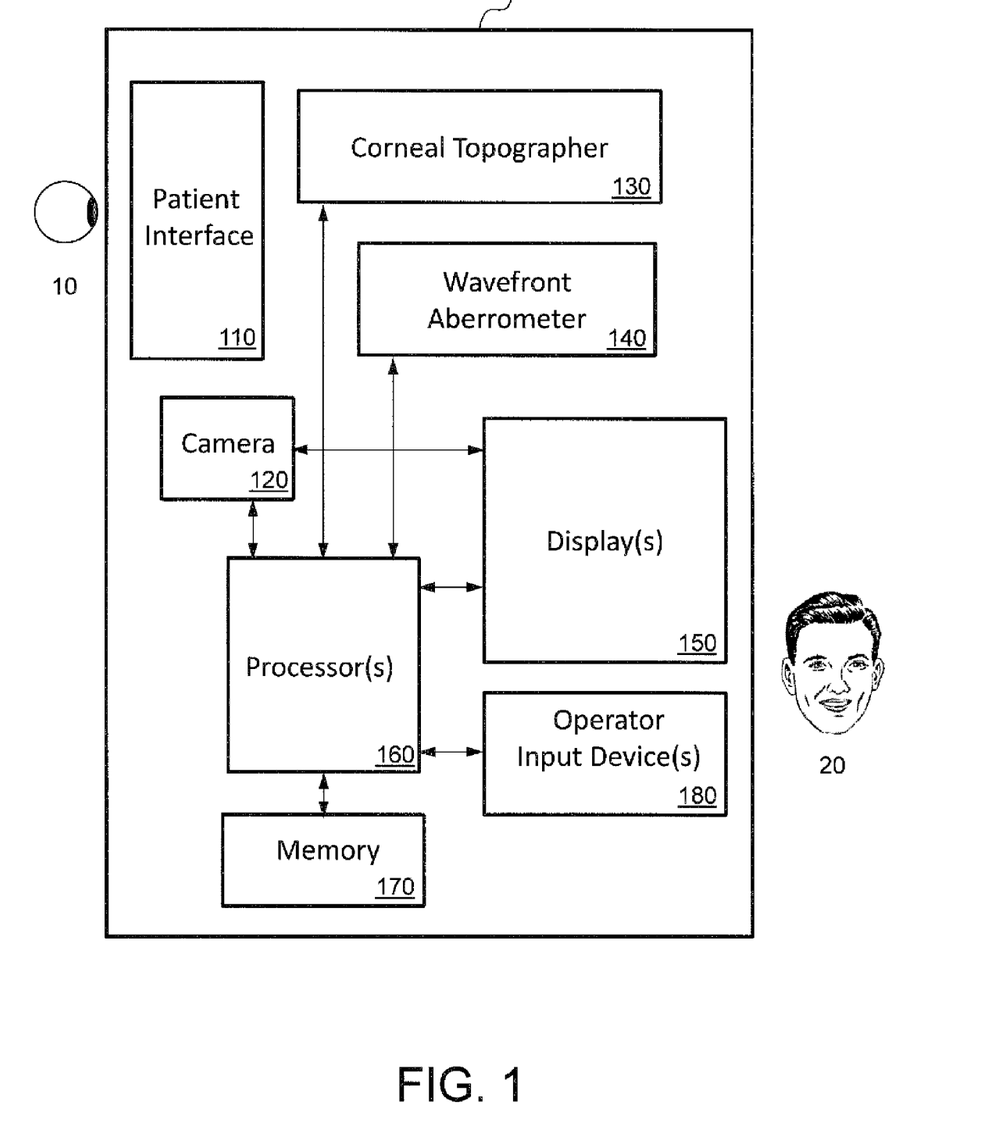
FIG. 1 is a functional block diagram of one embodiment of an optical measurement system.

FIG. 1 is a functional block diagram of one embodiment of an optical measurement instrument or optical measurement system 100 for measuring one or more characteristics of an eye 10. Optical measurement system 100 includes a patient interface (e.g., a headrest and eye examination area), a camera 120, a corneal topographer 130, a wavefront aberrometer 140, one or more displays 150, one or more processors 160 and associated storage (e.g., memory) 170, and one or more operator input devices 180 for receiving input or instructions from an operator 20. It should be understood that optical measurement system 100 is simply one embodiment for illustrating principles of the invention, and that many variations are possible which may omit certain elements, add additional elements, and/or change some of the elements. For example, another optical measurement system incorporating one or more aspects of this invention may omit corneal topographer 130 or wavefront aberrometer 140. Another optical measurement system may include only an autorefractor as a measurement instrument. Some implementations may include additional elements, for example one or more loudspeakers.

In some implementations, camera 120 may be an eye alignment camera which is used to insure proper eye alignment when making corneal topography and/or wavefront aberrometry measurements with corneal topographer 130 and/or wavefront aberrometer 140. In some implementations, camera 120 may be a separate camera which may be employed to determine when the subject blinks eye 10, for example in conjunction with a pattern recognition algorithm executed by processor(s) 160, as will be described in greater detail below. Beneficially, camera 120 alone or in conjunction with processor(s) 160 may provide a continuous live display of eye 10 to operator 20 via display 150.

Although example configurations of corneal topographer 130 and wavefront aberrometer 140 will be described in further detail below with respect to FIG. 2, it should be understood that these elements may employ any of a variety of other configurations.

Display(s) 150 may include one or more display devices which provide images and/or data to operator 20 under control of processor(s) 160. Such images and data may include operating instructions and/or requests for input from operator 20, images of eye 20 produced by camera 120, images and data reflecting measurements of eye 10 performed by corneal topographer 130 and/or wavefront aberrometer 140, etc. Display(s) 150 may include one or more flat panel displays, including one or more touchscreens, individual lights (e.g., light emitting diodes), or any other convenient display device(s).

Processor(s) 160 execute(s) computer-readable instructions for performing operations of optical measurement system 100. Such operations may include adjusting one or more operating parameters of corneal topographer 130 and/or wavefront aberrometer 140, processing data output by corneal topographer 130 and/or wavefront aberrometer 140, interpreting and responding to inputs and/or instructions received by operator input device(s) 180, generating images and/or data for display by display(s) 150, etc. Processor(s) may perform into operations using instructions and/or data stored in associated storage 170. Storage 170 may include any combination of volatile memory devices (e.g., random access memory), nonvolatile memory devices (e.g., read only memory, FLASH memory), computer readable media such as hard disk drives, optical disks, etc. In particular, storage 170 may store an operating system for processor(s) 160 and one or more computer programs which are executed by processor(s) 160 during operation of optical measurement system 100. In some implementations, storage 170 may store computer-readable instructions which cause processor(s) 160 to execute one or more algorithms for insuring that the tear film quality of a subject's eye satisfies some specified criterion or criteria when measuring one or more characteristics of the eye. In some implementations, storage 170 may store computer-readable instructions which cause processor(s) 160 to execute one or more algorithms described below with respect to FIGS. 6-8. In some implementations, storage 170 may store raw data produced by corneal topographer 130 and/or wavefront aberrometer 140, and/or data from corneal topographer 130 and/or wavefront aberrometer 140 which has been processed by processor(s) 160.

Operator input device(s) 180 may include any combination of the following devices: keyboard, touchscreen, touchpad, joystick, pushbuttons, roller ball, mouse, keypad, microphone, etc.

In general, processor(s) 160 operate in conjunction with display(s) 150 and operator input device(s) 180 to provide a user interface for receiving instructions and data from operator 20 and for communicating warnings, instructions, and data to operator 20.

Figure 2:
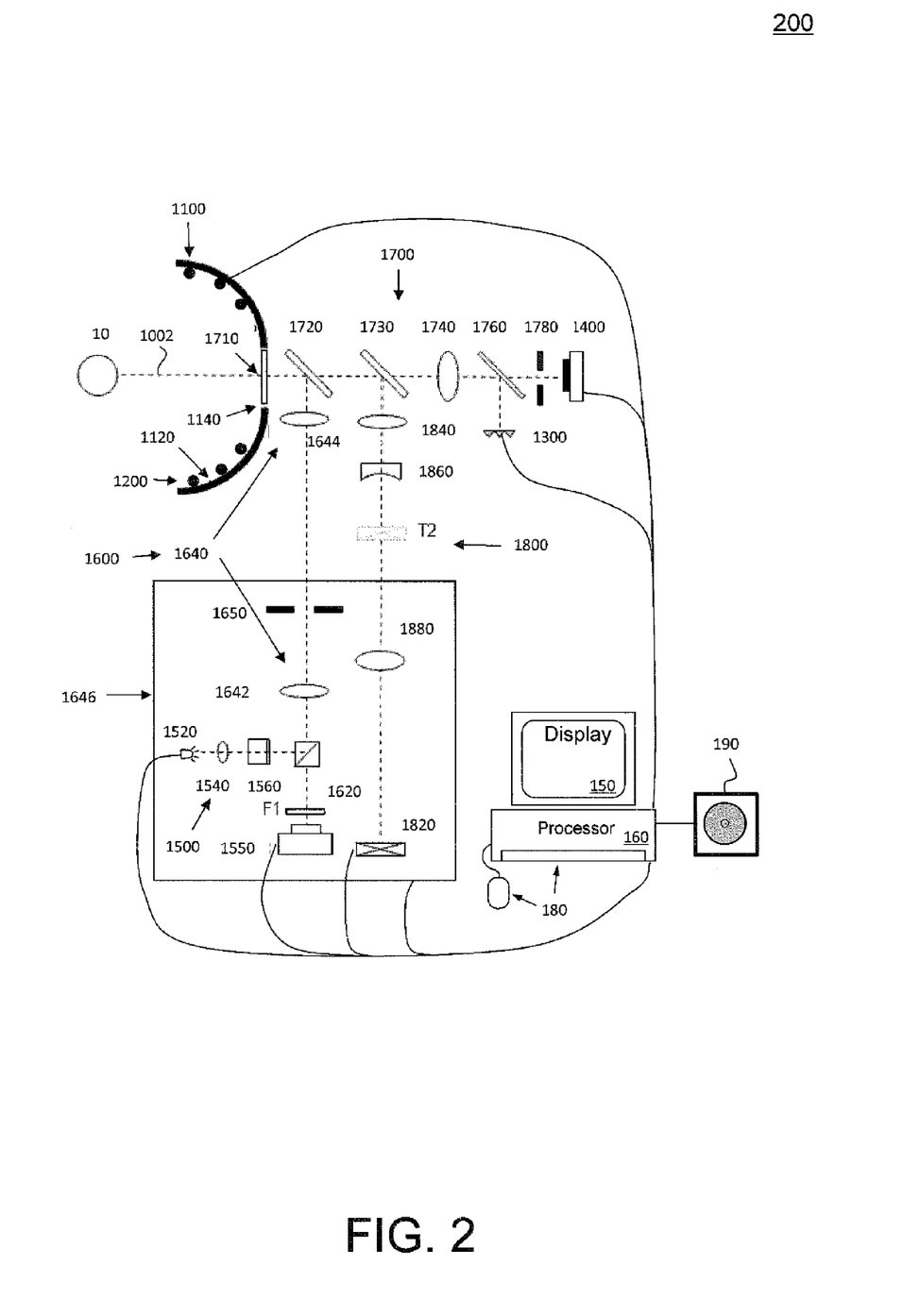
FIG. 2 is a more detailed diagram of portions of one embodiment of an optical measurement system.

FIG. 2 is a more detailed diagram of portions of one embodiment of an optical measurement instrument or optical measurement system 200. System 200 comprises a structure 1100 having a principal surface 1120 with an opening or aperture 1140 therein; a plurality of first (or peripheral) light sources 1200 provided on the principal surface 1120 of the structure 1100; a plurality of second, or central, light sources 1300 (sometimes referred to as "Helmholtz light sources"); a detector array 1400; a display 150; a processor 160; operator input devices 180; a third light source 1500 providing a probe beam; a wavefront sensor 1550; and an optical system 1700 disposed along a central axis 1002 passing through the opening or aperture 1140 of the structure 1100. Optical system 1700 comprises a quarterwave plate 1710, a first beamsplitter 1720, a second beamsplitter 1730, an optical element (e.g., a lens) 1740, a third beamsplitter 1760, and a structure including an aperture 1780. Beneficially, third light source 1500 includes a lamp 1520, a collimating lens 1540, and light source polarizing beamsplitter 1560. Associated with third light source 1500 and wavefront sensor 1550 in a wavefront analysis system 1600 also comprising: a polarizing beamsplitter 1620; an adjustable telescope 1640 comprising a first optical element (e.g., lens) 1642 and a second optical element (e.g., lens) 1644 and a movable stage or platform 1646; and a dynamic-range limiting aperture 1650 for limiting a dynamic range of light provided to wavefront sensor 1550. It will be appreciated by those of skill in the art that the lenses 1642, 1644, or any of the other lenses discussed herein, may be replaced or supplemented by another type of converging or diverging optical element, such as a diffractive optical element. Beneficially, system 200 further comprises a fixation target system 1800, comprising light source 1820 and lenses 1840, 1860, and 1880.

As used herein the term "light source" means a source of electromagnetic radiation, particularly a source in or near the visible band of the electromagnetic spectrum, for example, in the infrared, near infrared, or ultraviolet bands of the electromagnetic radiation. As used herein, the term "light" may be extended to mean electromagnetic radiation in or near the visible band of the electromagnetic spectrum, for example, in the infrared, near infrared, or ultraviolet bands of the electromagnetic radiation.

In one implementation, structure 1100 has the shape of an elongated oval or "zeppelin" with openings or apertures at either end thereof. An example of such a structure is disclosed in Meji'a-Barbosa, cited above, as particularly illustrated in FIG. 4 therein. In some implementations, principal surface 1120 of structure 1100 is concave when viewed from the cornea of eye 10, as illustrated in FIG. 2.

In one implementation where principal surface 1120 is concave, principal surface 1120 may have the shape of a conical frustum. Alternatively, principal surface 1120 may have a shape of a hemisphere or some other portion of a sphere, with an opening or aperture therein. Also alternatively, principal surface 1120 may have the shape of a modified sphere or conical frustum, with a side portion removed. Beneficially, such an arrangement may improve the ergonomics of system 200, particularly the patient interface (element 110 in FIG. 1) by more easily allowing structure 1100 to be more closely located to eye 10 without being obstructed by the subject's nose. Of course, a variety of other configurations and shapes for principal surface 1120 are possible.

In the embodiment of FIG. 2, the plurality of first light sources 1200 are provided on the principal surface 1120 of structure 1100 so as to illuminate the cornea of eye 10. In one implementation, light sources 1220 may comprise individual light generating elements or lamps, such as light emitting diodes (LEDs) and/or the tips of the individual optical fibers of a fiber bundle. Alternatively, principal surface 1120 of structure 1100 may have a plurality of holes or apertures therein, and one or more backlight lamps, which may include reflectors and/or diffusers, may be provided for passing lighting through the holes to form the plurality of first light sources 1200 which project light onto the cornea of eye 10. Other arrangements are possible.

In another implementation, structure 1100 is omitted from system 200, and the first light sources 1200 may be independently suspended (e.g., as separate optical fibers) to form a group of first light sources 1200 arranged around a central axis, the group being separated from the axis by a radial distance defining an aperture in the group (corresponding generally to the aperture 1140 in the structure 1100 illustrated in FIG. 2).

In one implementation, second light sources 1300 comprise a plurality of lamps, such as LEDs or optical fiber tips. Alternatively, second light sources 1300 may comprise a plurality of holes or apertures in a surface that are illuminated by one or more backlight lamps with reflectors and/or diffusers.

In one implementation, second light sources 1300 are located off the central optical axis 1002 of system 200, and light from second light sources is directed toward optical element 1740 by third beamsplitter 1760. Alternatively, second light sources 1300 may comprise a plurality of lamps disposed on the structure around the aperture 1780, perpendicular to the optical axis 1002.

Beneficially, each of the second light sources 1300 is located approximately one focal length, f, away from optical element 1740.

Detector array 1400 comprises a plurality of light detecting elements arranged in a two dimensional array. In one implementation, detector array 1400 comprises such a charge-coupled device (CCD), such as may be found in a video camera. However, other arrangements such as a CMOS array, or another electronic photosensitive device, may be employed instead. Beneficially, the video output signal(s) of detector array 1400 are provided to processor(s) 160 which processes these output signals according to known algorithms to produce corneal topography for eye 10.

Beneficially, lamp 1520 of third light source 1500 is an 840 nm SLD (super luminescent laser diode).

Beneficially, wavefront sensor 1550 may be Shack-Hartmann wavefront sensor comprising a detector array and a plurality of lenslets for focusing received light onto its detector array. In that case, the detector array may be a CCD, a CMOS array, or another electronic photosensitive device. Embodiments of wavefront sensors which may be employed in one or more systems described herein are described in U.S. Pat. No. 6,550,917, issued to Neal et al. on Apr. 22, 2003, and U.S. Pat. No. 5,777,719, issued to Williams et al. on Jul. 7, 1998, both of which patents are hereby incorporated herein by reference in their entirety. However, other wavefront sensors may be employed instead.

Wavefront sensor 1550 outputs signals to processor(s) 160 which use(s) the signals to determine ocular aberrations of eye 10. Beneficially, processor(s) 160 is/are able to better characterize eye 10 by considering the corneal topography of eye 10, which may also be determined by processor(s) 160 based on outputs of detector array 1400, as explained above.

The configurations and operation of display 150, processor 160, and operator input devices 180 have been described above with respect to FIG. 1, and will not be repeated.

As shown in FIG. 2, optical measurement system 200 further includes a loudspeaker 190 which may provide audible warnings, instructions and/or other audible feedback to operator 20.

Although not shown in FIG. 2, optical measurement system 200 further includes one or more eye illumination sources and camera 120 for capturing images of a subject's eye 10.

Further details of various example implementations of optical measurement system 200 may be found in U.S. Pat. No. 7,976,163, which is incorporated herein by reference.

As explained above, any measurements of the eye which are made when the tear film has degraded will not reflect the normal optical performance of the eye. More specifically, if the corneal topography and/or refraction of the eye are measured under such a condition where the tear layer has been disrupted, the measurements will be in error.

Accordingly, optical measurement systems 100 and 200 execute one or more algorithms to insure that the that the tear film quality of a subject's eye 10 satisfies some specified criterion or criteria when measuring one or more characteristics of eye 10. An explanation of various embodiments of such algorithms will be described now with respect to optical measurement system 100, but it should be understood that these descriptions also may be applied to optical measurement system 200.

In some implementations, optical measurement system 100 receives from operator 20, via the user interface (e.g., operator input devices 180) of optical measurement system 100, a begin measurement instruction indicating the start of a measurement period for objectively measuring at least one characteristic of the subject's eye 10. Subsequent to receiving the begin measurement instruction, optical measurement system 100 determines whether or not a criterion or criteria associated with the tear film quality of the subject's eye 10 is/are satisfied. In response to determining that the criterion/criteria is/are not satisfied, optical measurement system 100 takes one or more corrective actions so as to measure the characteristic of the subject's eye 10 under conditions where the criterion/criteria is/are satisfied.

In some implementations, optical measurement system 100 may determine the tear film quality of the subject's eye 10 directly. In such implementations, processor(s) 160 may analyze wavefront data output from wavefront aberrometer 140 to determine that the tear film quality is not within acceptable parameters, and in that case may take one or more corrective actions (e.g., prompt operator 20 to instruct the subject to blink) and then recommence the wavefront measurement(s). For example, when light spots on the detector of wavefront aberrometer 140 do not conform to expected standards, for example due to missing light spots or light spots which are too large, etc., optical measurement system 100 may determine that the tear film quality is not within acceptable parameters. In some implementations, optical measurement system 100 may determine the thinness of the tear film and/or a breakup of the tear film and use one or both of these as criteria for evaluating the tear film quality of a subject's eye 10. For example, in some implementations optical measurement system may specify a quality threshold for the tear film based on the thinness of the tear films and/or an amount of tear film break-up which is detected, and may take one or more corrective actions as described below when the tear film quality does not meet or exceed the specified quality threshold Processor(s) 160 may employ any of a variety of analysis algorithms and associated criteria to make the determination of tear film quality.

The inventors have appreciated that the tear film quality of a subject's eye 10 may be related to the time interval between blinks of eye 10. The inventors have further appreciated that tear film can generally be assumed to be stable and of sufficient quality to make accurate eye measurements when a subject blinks eye 10 within a "normal" time interval, and that after such a normal time interval the tear film may break up for some people. For example, eight seconds may be considered to be a "normal" time interval, and the tear film quality can be assumed to be of acceptable quality any time within eight seconds of the last time the subject blinked. On the other hand, about 50% of subjects will have the tear film start to break up if blinks are more than 12 seconds apart. Also, a typical blink rate for normal visual conditions is about 12 blinks per minute, which decreases to about five blinks per minute when a person is reading. Many people will complain of eye discomfort if the time between blinks exceeds 10-12 seconds. It should be understood that the "normal" time interval is a statistical value for a large number of subjects, and what may be normal for any particular subject, and what blink rates lead to tear film degradation for any particular subject, may vary substantially from these numbers.

Accordingly, in some implementations, optical measurement system 100 may determine whether or not a criterion or criteria associated with the tear film quality of the subject's eye 10 is/are satisfied by determining whether an elapsed time period associated with the subject blinking exceeds a threshold, and, in response to determining that the elapsed time period associated with the subject blinking exceeds the threshold, take one or more corrective actions. For example, optical measurement system 100 may determine a time interval from the time when the measurements were begun and/or the last time when the subject blinked eye 10, and when that time interval exceeds a threshold (e.g., 8 seconds or 12 seconds), optical measurement system 100 may provide an indication to operator 20 that the subject should blink eye 10.

In some implementations, optical measurement system 100 may determine when a subject blinks eye 10 by receiving an input from operator 20 via the user interface indicating that the subject blinked eye 10.

In some implementations, optical measurement system 100 may determine when a subject blinks eye 10 by capturing a series of images of the subject's eye 10, detecting from the captured images a blink of the subject's eye 10. In some implementations, processor(s) 160 may employ pattern recognition software to detect when the subject's eye 10 blinks. In some implementations, processor(s) 160 may execute an algorithm similar to algorithms employed by automatic drowsy-driver detection systems which detect eye blinks by vehicle drivers to determine when the driver has fallen asleep or is no longer awake. An example of such an algorithm is described in "*Drowsy Detection On Eye Blink Duration Using Algorithm*," Mandeep Singh et al., INTERNATIONAL JOURNAL OF EMERGING TECHNOLOGY AND ADVANCED ENGINEERING, Vol. 2, No. 4, April 2012.

In some implementations, the series of images of the subject's eye 20 are captured by camera 120 and camera 120 is an eye alignment camera of optical measurement system 100. In other implementations, camera 120 is a second camera of optical measurement system 100 separate from an eye alignment camera of optical measurement system 100. In that case, camera 120 may have a wider field of view and/or a longer depth of field than the eye alignment camera.

In some implementations, optical measurement system 100 may provide an indication or instruction to operator 20 via the interface that the operator should ask the user to blink before commencing measurements. In response to the indication via the user interface to the operator 20 that the subject should blink, operator 20 may instruct the subject to blink, and then provide an instruction to optical measurement system 100 to begin the measurement of one or more characteristics of eye 10 (for example, by clicking on a "start measurement" button displayed on display 150). Optical measurement system 100 may start a timer (e.g., a timer of processor(s) 160) to measure an elapsed time interval from the start time when the "begin measurement" instruction is received from user 20 via the user interface.

When the time interval exceeds a defined threshold maximum time interval (e.g., 8 seconds or 12 seconds), then optical measurement system 100 may take one or more corrective actions. These corrective actions may include stopping further measurements until the tear film quality is determined to have improved to an acceptable level, discarding any measurements made when the time interval between blinks has been exceeded and only retain and process measurements made within the defined threshold maximum time interval, and/or providing an indication to operator 20 via the user interface that the subject should blink.

In some implementations, after providing an indication to operator 20 via the user interface that the subject should blink, optical measurement system 100 may restart or reset the time interval between blinks after either detecting a blink automatically via camera 120 and processor(s) 160, as described above, or in response to an input received from operator 20 via the user interface indicating that the subject has blinked.

In some implementations, optical measurement system 100, and particularly processor(s) 160, may employ a combination of the blink detection algorithms described above and/or the tear film quality detection algorithms described above to determine whether or not the tear film quality of the subject's eye 10 satisfies the specified criterion or criteria when measuring one or more characteristics of eye 10. When the tear film quality does not satisfy the specified criterion or criteria, then optical measurement system 100, and particularly processor(s) 160, may take one or more corrective actions as described above, including stopping further measurements until the tear film quality is determined to have improved to an acceptable level, discarding any measurements made when the tear film quality is unacceptable and only retain and process measurements made within the tear film quality is deemed acceptable, and/or providing an indication to operator 20 via the user interface that the subject should blink. In some implementations, processor (s) 160 of optical measurement system 100 may store eye blink data or an eye blink record in storage 170 which includes a record of the history of the subject's blinks of eye 10 during the time when measurements of eye are made. In some implementations, the eye blink data or record may be associated in storage 170 with the corresponding data produced by optical measurement system 100 from the measurements of eye 10. For example a patient record for a subject may be stored in storage 170 and include the objective measurement data, measurement conditions (e.g., measurement date, operator, etc.), one or more eye images, the blink history, personal identification data, and other relevant data pertaining to the subject, etc.

In some implementations, the indication to operator 20 that the subject should blink may be provided as a text message on display 150.

In some implementations, the indication to operator 20 that the subject should blink may be provided as an audible signal via a loudspeaker.

In some implementations, the indication to operator 20 that the subject should blink is provided via a progress bar displayed on a display 150 of optical measurement system 100. In that case, the progress bar is reset to zero when optical measurement system 100 determines that the subject blinks, as explained above.

Figure 3A:
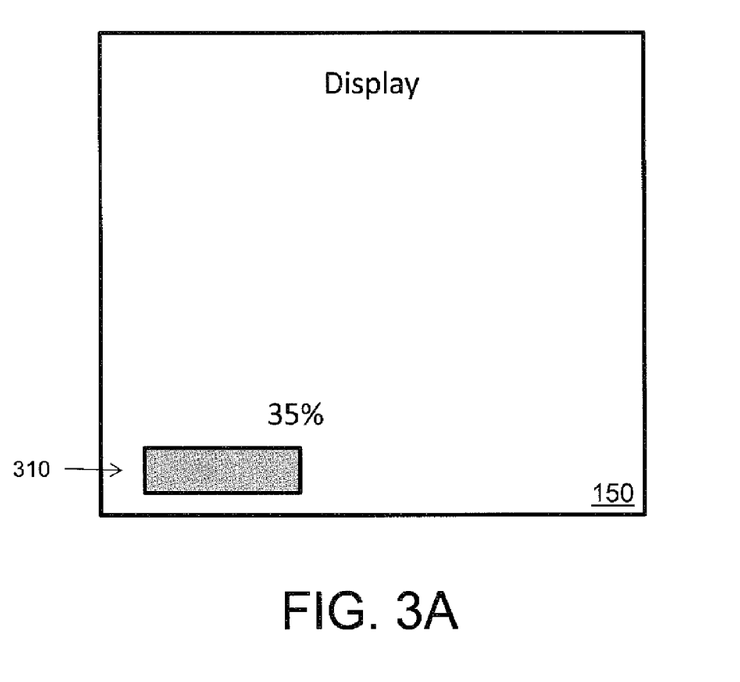
FIG. 3A and FIG. 3B illustrate a first example embodiment of a progress bar for indicating an elapsed time period associated with the subject blinking.
Figure 3B:
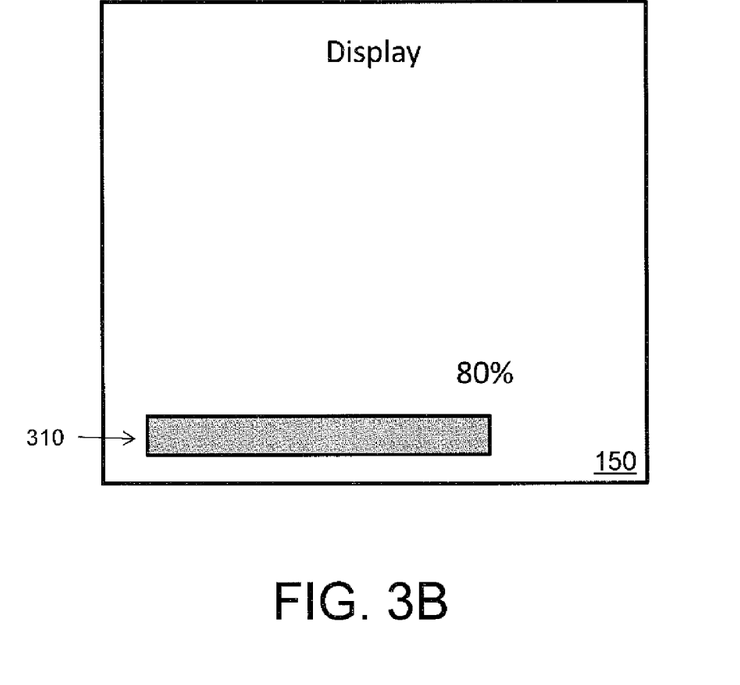

FIG. 3A and FIG. 3B illustrate a first example embodiment of a progress bar 310 for indicating to user 20 an elapsed time period associated with the subject blinking. Progress bar 310 displays a percentage from 0% to 100% based on the relationship between the time interval from the last time that the subject blinked and a specified maximum time interval between blinks which is set by software of optical measurement system 100. In some implementations, the specified maximum time interval between blinks may be between 8 and 12 seconds. For example, in some implementations, the specified maximum time interval between blinks may be 8 seconds. In other implementations, the specified maximum time interval between blinks may be 12 seconds. However, it should be understood that other specified maximum time interval between blinks may be employed, and that the specified maximum time interval between blinks may be varied from subject to subject. In some implementations, once progress bar 310 reached 100%, its color may change (from example, from green to red) and/or it may begin to blink to draw the attention of operator 20.

Here, progress bar 310 is displayed horizontally, but of course it could be displayed vertically.

In response to detecting a blink of subject's eye 10, optical measurement system 100 restarts the time interval for measuring when the subject last blinked, as described above, and resets progress bar 310 back to 0%.

Figure 4A:
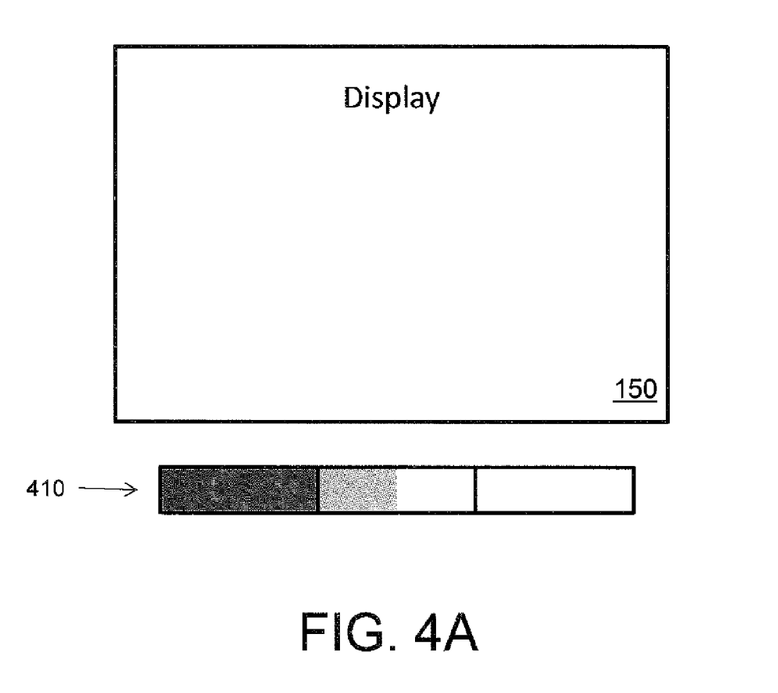
FIG. 4A and FIG. 4B illustrate a second example embodiment of a progress bar for indicating an elapsed time period associated with the subject blinking.
Figure 4B:
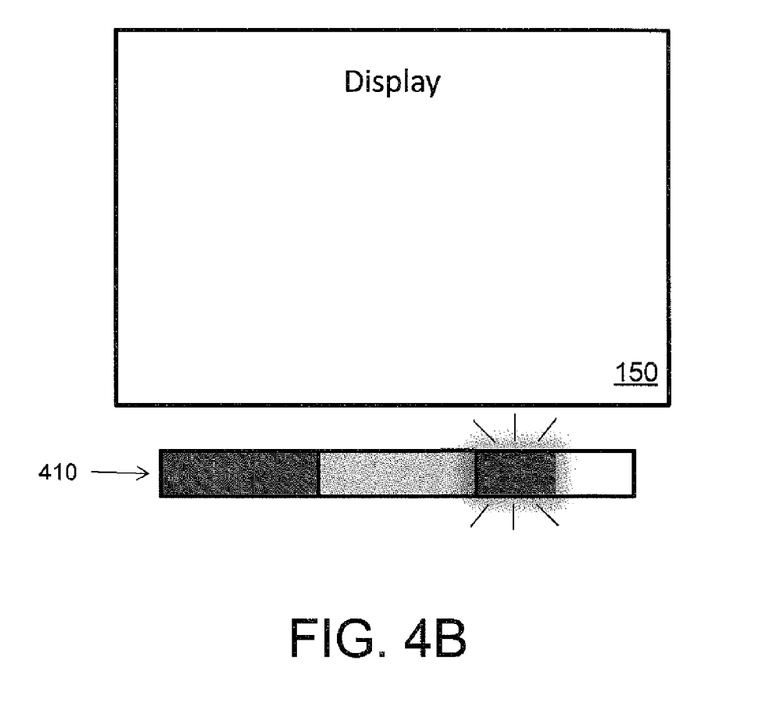

FIG. 4A and FIG. 4B illustrate a second example embodiment of a progress bar 410 for indicating an elapsed time period associated with the subject blinking. Here, a first portion (e.g., a first third) of progress bar 410 is displayed in a first color (e.g., green), a second portion (e.g., a second third) of progress bar 410 is displayed in a second color (e.g., yellow), and a third portion (e.g., a last third) of progress bar 410 is displayed in a third color (e.g., color).

Progress bar 410 may represent a specified maximum time interval between blinks which is set by software of optical measurement system 100. In some implementations, the specified maximum time interval between blinks may be between 8 and 12 seconds. For example, in some implementations, the specified maximum time interval between blinks may be 8 seconds. In other implementations, the specified maximum time interval between blinks may be 12 seconds. In some implementations, once progress bar 410 has reached its end, the color of one or all of the segments may change (from example, to all red) and/or it may begin to blink to draw the attention of operator 20.

Here, progress bar 410 is displayed horizontally, but of course it could be displayed vertically.

In response to detecting a blink of subject's eye 10, optical measurement system 100 restarts the time interval for measuring when the subject last blinked, as described above, and resets progress bar 410 back to the beginning.

Figure 5A:
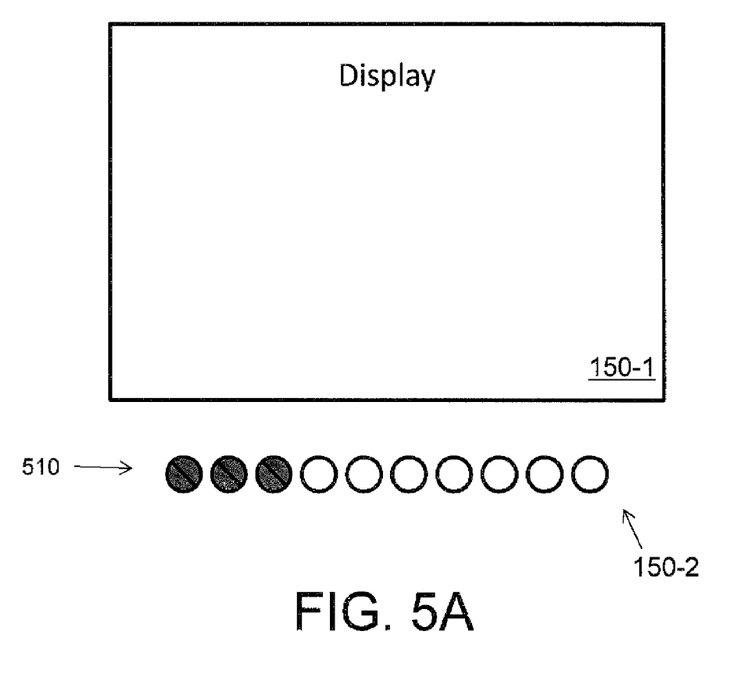
FIG. 5A and FIG. 5B illustrate a third example embodiment of a progress bar for indicating an elapsed time period associated with the subject blinking.
Figure 5B:
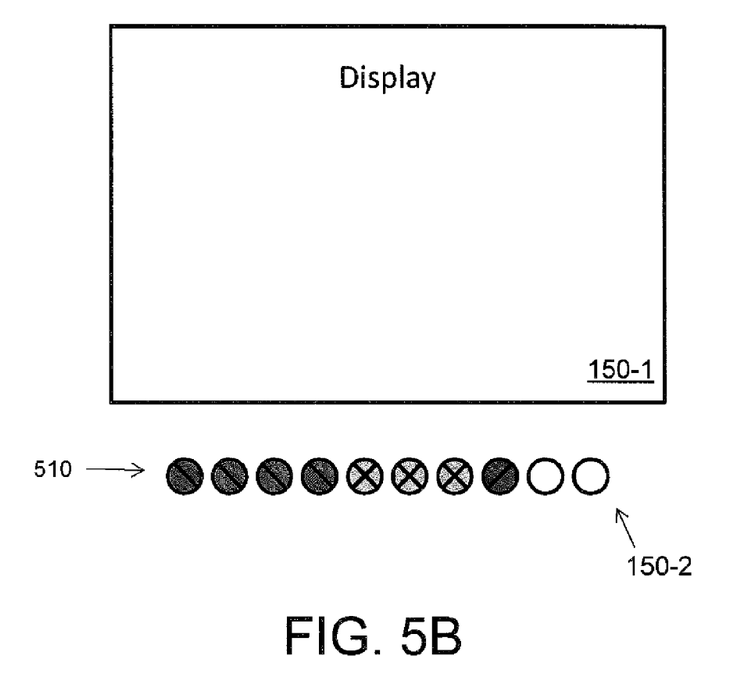

FIG. 5A and FIG. 5B illustrate a third example embodiment of a progress bar 610 for indicating an elapsed time period associated with the subject blinking. Here, optical measurement system 100 includes a first display 150-1 and a second display 150-2 which comprises a group of individual light elements (e.g., light emitting diodes (LEDs)). Here, second display 150-2 comprises ten LEDs arranged horizontally, but of course any number of LEDs may be included, and the LEDs could be arranged vertically. Progress bar 610 is displayed via second display 150-2. In this example, the first four LEDs are green, the next three LEDs are yellow, and the last three LEDs are red. Again, any combination of colored elements may be employed.

Progress bar 510 may represent a specified maximum time interval between blinks which is set by software of optical measurement system 100. In some implementations, the specified maximum time interval between blinks may be between 8 and 12 seconds. For example, in some implementations, the specified maximum time interval between blinks may be 8 seconds. In other implementations, the specified maximum time interval between blinks may be 12 seconds. In this example where there are ten LEDs, each LED may represent 10% of the specified maximum time interval between blinks. In that case, another LED may be illuminated every time that the time interval reaches another 10% of the specified maximum time interval, until all ten LEDs are illuminated, or until the time interval is reset by the subject blinking. In some implementations, once progress bar 510 has reached its end, the color of one or all of the elements may change (from example, to all red) and/or the elements begin to blink to draw the attention of operator 20.

In response to detecting a blink of subject's eye 10, optical measurement system 100 restarts the time interval for measuring when the subject last blinked, as described above, and resets progress bar 510 back to the beginning, turning off all of the LEDs.

FIGS. 3-5 illustrate a few example embodiments of progress bar for optical measurement system 100 which may have certain beneficial features, but it should be understood that in general a progress bar having any desired configuration may be employed.

In some implementations, the indication to operator 20 that the subject should blink may be provided by various combinations of the text message, progress bar, and audible signals described above.

In some cases, it is possible that the tear film may be degraded due to the subject holding eye 10 open too long while staring into optical measurement system 100, leading to excessive watering of eye 10. In that case, in some implementations optical measurement system 100 may employ a tear film quality criterion which includes determining whether the subject's eye exhibits excessive tearing. For example, in some implementations excessive tearing may be detected by pattern recognition of shimmering reflections of the eye illumination light source(s) as seen by camera 120. In that case, a corrective action taken by optical measurement system 100 in response to determining that the subject's eye exhibits excessive tearing, may be to delay objective measurement of the characteristic(s) of the subject's eye 10 by a specified delay period (e.g., two or three seconds) to allow the tearing to dissipate. Another corrective action may be to discard any measurements made when there is excessive tearing, and only retain and process measurements when the tear film quality is acceptable.

Figure 6:
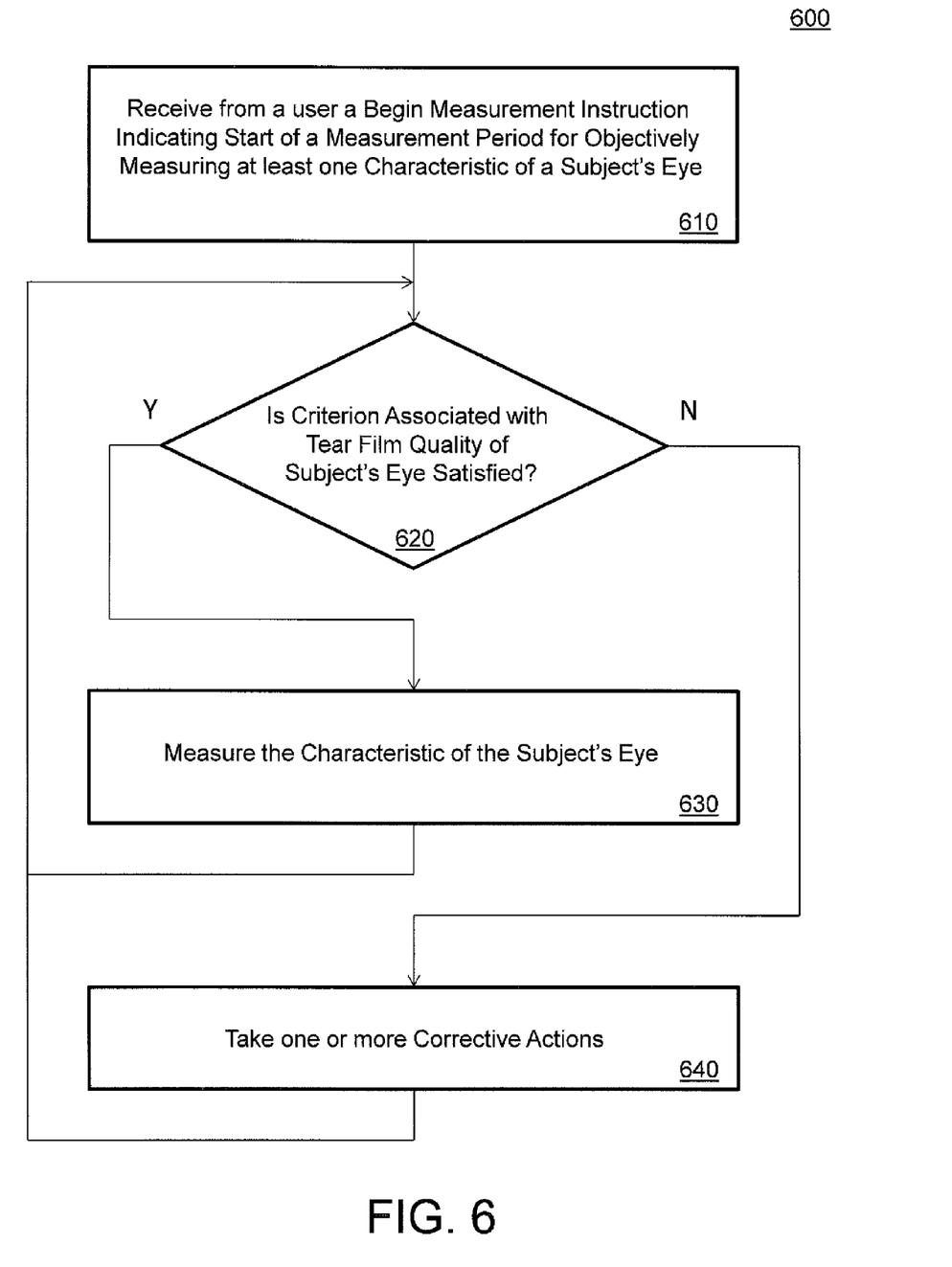
FIG. 6 illustrates a first example embodiment of a process of insuring that a tear film quality criterion is satisfied when measuring a characteristic of a subject's eye.

FIG. 6 illustrates a first example embodiment of a method or process 600 of insuring that the tear film quality criterion is satisfied when measuring a characteristic of a subject's eye. In some implementations, optical measurement systems 100 and/or 200 may employ process 600.

Process 600 includes an operation 610. In operation 610, the optical measurement system receives from a user via a user interface a Begin Measurement instruction indicating the start of a measurement period for objectively measuring at least one characteristic of a subject's eye.

In operation 620, the optical measurement instrument determines whether one or more criterion associated with the tear film quality of the subject's eye is satisfied. If the criterion/criteria is/are satisfied, then the process proceeds to operation 630. Otherwise, the process proceeds to operation 640.

In operation 630, the optical measurement system continues to objectively measure one or more characteristics of the subject's eye (e.g., via corneal topography and/or wavefront aberrometry). As the measurement(s) proceed(s), operation 620 is repeated.

In operation 640, the optical measurement system takes one or more corrective actions to measure the characteristic(s) of the subject's eye under a condition wherein the criterion or criteria are satisfied. The corrective actions may include stopping further measurements until the tear film quality is determined to have improved to an acceptable level, and/or providing an indication to the operator of the optical measurement system via the user interface that the subject should blink.

Figure 7:
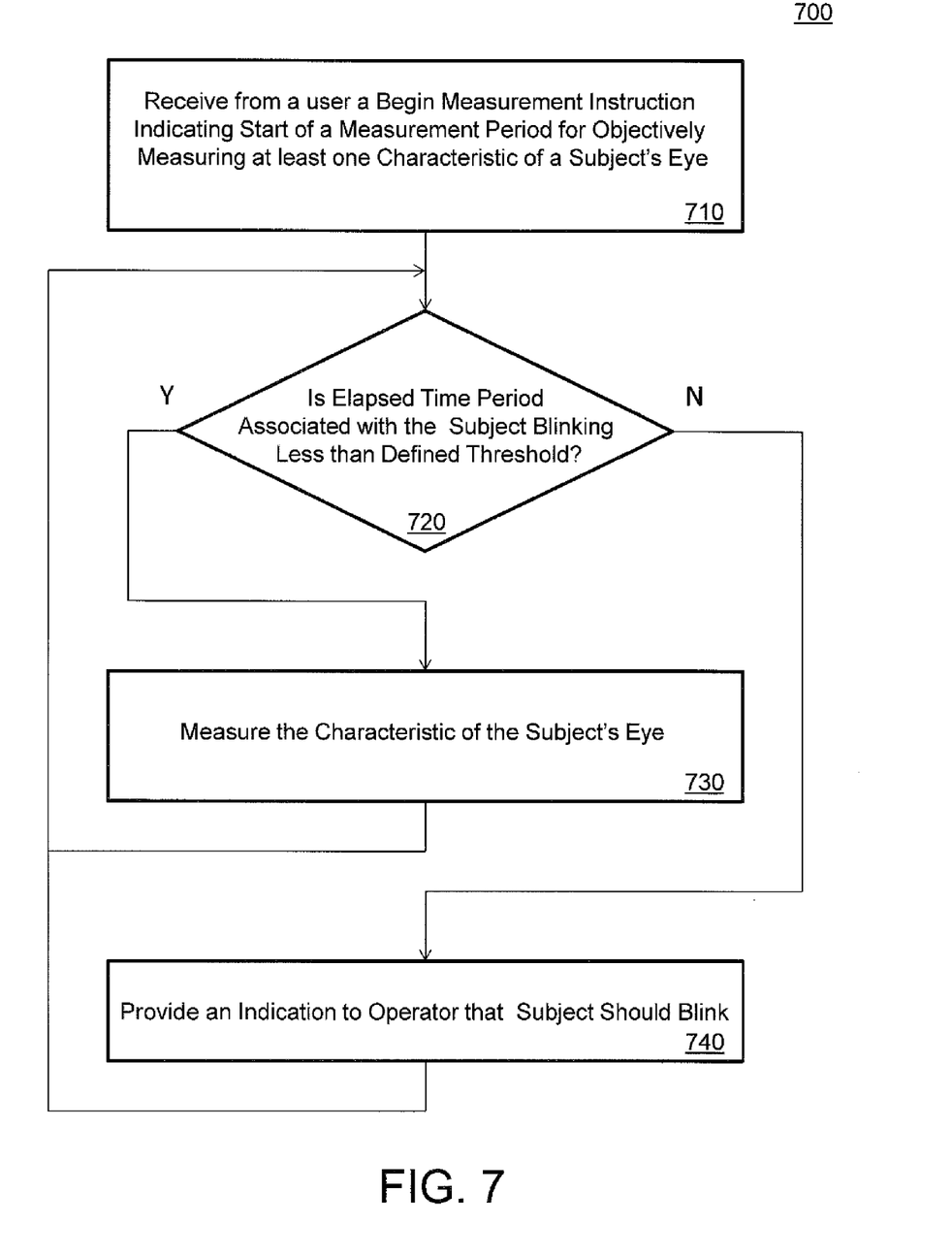
FIG. 7 illustrates a second example embodiment of a process of insuring that a tear film quality criterion is satisfied when measuring a characteristic of a subject's eye.

FIG. 7 illustrates a second example embodiment of a method or process 700 of insuring that a tear film quality criterion is satisfied when measuring a characteristic of a subject's eye. In some implementations, optical measurement systems 100 and/or 200 may employ process 700.

Process 700 includes an operation 710. In operation 710, the optical measurement system receives from a user via a user interface a Begin Measurement instruction indicating the start of a measurement period for objectively measuring at least one characteristic of a subject's eye.

In operation 720, the optical measurement instrument determines whether an elapsed time period associated with the subject blinking is less than a defined threshold. For example, in some implementations, the optical measurement instrument determines whether a time interval measured from the last time that the subject blinks is less than a specified maximum time interval between blinks. If the criterion/criteria is/are satisfied, then the process proceeds to operation 730. Otherwise, the process proceeds to operation 740.

In operation 730, the optical measurement system continues to objectively measure one or more characteristics of the subject's eye (e.g., via corneal topography and/or wavefront aberrometry). As the measurement(s) proceed(s), operation 720 is repeated.

In operation 740, the optical measurement system provides an indication to the operator of the optical measurement system via the user interface that the subject should blink.

Figure 8:
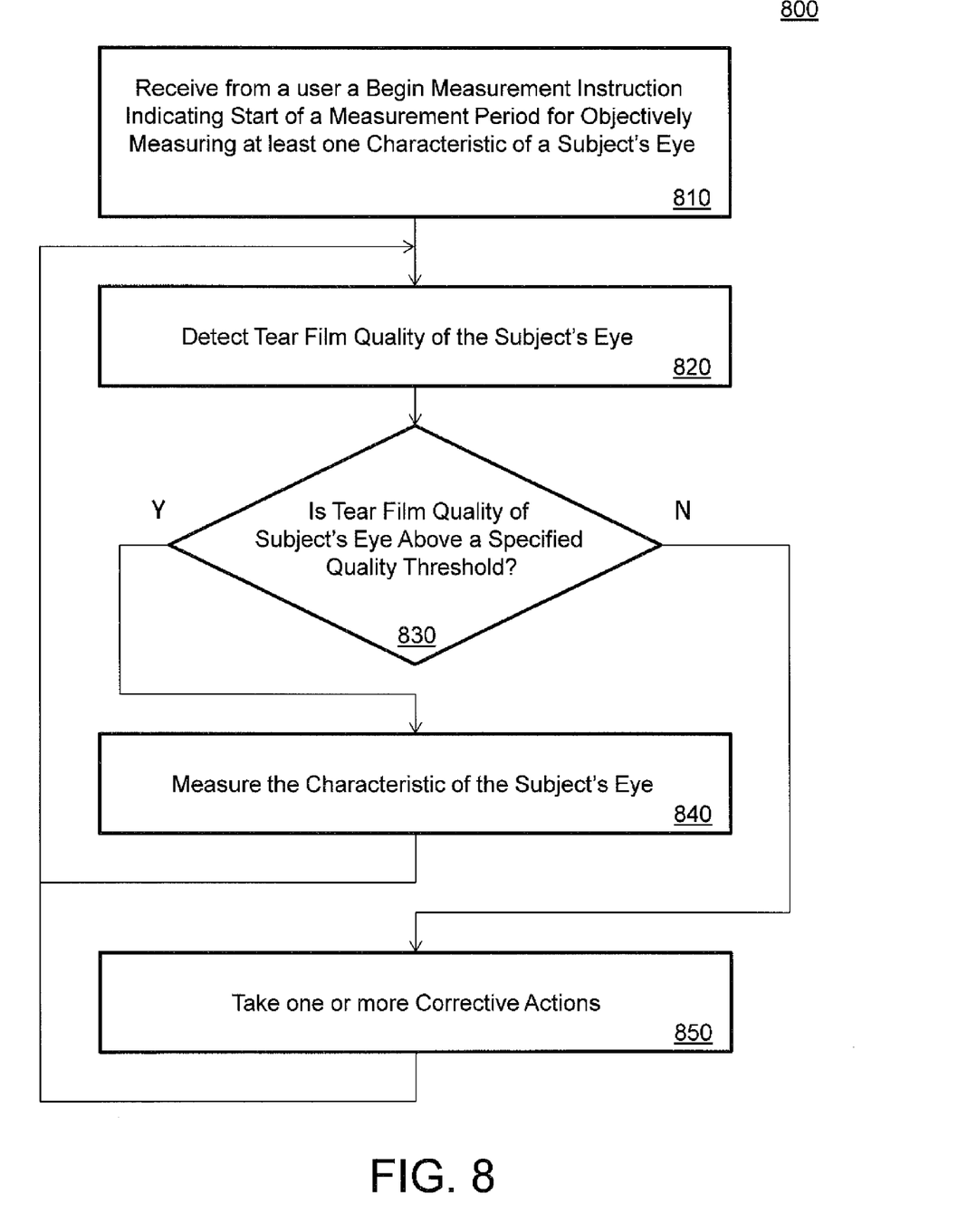
FIG. 8 illustrates a third example embodiment of a process of insuring that a tear film quality criterion is satisfied when measuring a characteristic of a subject's eye.

FIG. 8 illustrates a third example embodiment of a method or process 800 of insuring that a tear film quality criterion is satisfied when measuring a characteristic of a subject's eye. In some implementations, optical measurement systems 100 and/or 200 may employ process 800.

Process 800 includes an operation 810. In operation 810, the optical measurement system receives from a user via a user interface a Begin Measurement instruction indicating the start of a measurement period for objectively measuring at least one characteristic of a subject's eye.

In operation 820, the optical measurement system detects the tear film quality for the subject's eye. As explained above, in various implementations this may include determining the thinness of the tear film and/or an amount of percentage of breakup of the tear film.

In operation 830, the optical measurement instrument determines whether or not the tear film quality of the subject's eye meets a specified quality threshold. If the specified quality threshold is met or exceeded, then the process proceeds to operation 840. Otherwise, the process proceeds to operation 850.

In operation 840, the optical measurement system continues to objectively measure one or more characteristics of the subject's eye (e.g., via corneal topography and/or wavefront aberrometry). As the measurement(s) proceed(s), operation 620 is repeated.

In operation 850, the optical measurement system takes one or more corrective actions to measure the characteristic(s) of the subject's eye under a condition wherein the criterion or criteria are satisfied. The corrective actions may include stopping further measurements until the tear film quality is determined to have improved to an acceptable level, and/or providing an indication to the operator of the optical measurement system via the user interface that the subject should blink.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Other variations are within the concept, scope, or spirit of the present invention. While the invention is susceptible to various modifications and alternative constructions, certain illustrated embodiments of the invention are shown in the drawings, and have been described above in an exemplary form with a certain degree of particularly. Those of ordinary skill in the art will understand, however, that the embodiments are provided by way of example only, and that various variations can be made without departing from the spirit or scope of the invention. Thus, there is no intention to limit the invention to the specific form or forms disclosed. Rather, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

We claim:

1. A method for measuring a characteristic of a subject's eye, the method comprising:
   an optical measurement instrument receiving from an operator, via a user interface of the optical measurement instrument, a begin measurement instruction indicating the start of a measurement period for objectively measuring at least one characteristic of the subject's eye;
   subsequent to receiving the begin measurement instruction, determining whether a criterion associated with the tear film quality of the subject's eye is not satisfied, which comprises determining whether an elapsed time period associated with the subject blinking exceeds a threshold; and
   in response to determining that the criterion is not satisfied, taking one or more corrective actions to measure the characteristic of the subject's eye under a condition wherein the criterion is satisfied, which comprises, in response to determining that the elapsed time period associated with the subject blinking exceeds the threshold providing an indication via the user interface to the operator that the subject should blink.

2. The method of claim 1, wherein determining whether the elapsed time period associated with the subject blinking does not exceed a threshold comprises measuring a time interval from a last time when the subject last blinked.

3. The method of claim 2, further comprising:
   capturing a series of images of the subject's eye;
   detecting from the captured images a blink of the subject's eye; and
   in response to detecting a blink of the subject's eye, resetting the time interval.

4. The method of claim 3, wherein the series of images of the subject's eye are captured by an eye alignment camera of the optical measurement instrument.

5. The method of claim 3, wherein the series of images of the subject's eye are captured by a second camera of the optical measurement instrument separate from an eye alignment camera of the optical measurement instrument, wherein the second camera has a wider field of view and longer depth of field than the eye alignment camera.

6. The method of claim 1, wherein determining whether the elapsed time period associated with the subject blinking does not exceed a threshold comprises measuring the elapsed time period from a start time corresponding to a time when the begin measurement instruction is received by the optical measurement instrument.

7. The method of claim 6, further comprising receiving from the operator via the user interface another begin measurement instruction in response to the indication via the user interface to the operator that the subject should blink.

8. The method of claim 1, wherein the indication to the operator that the subject should blink comprises a progress bar displayed on a display device of the optical measurement instrument, the progress bar being reset to zero when the subject blinks.

9. The method of claim 8, wherein the progress bar changes color to indicate when the elapsed time period exceeds the threshold.

10. A method for measuring a characteristic of a subject's eye, the method comprising:
    an optical measurement instrument receiving from an operator, via a user interface of the optical measurement instrument, a begin measurement instruction indicating the start of a measurement period for objectively measuring at least one characteristic of the subject's eye;
    subsequent to receiving the begin measurement instruction, determining whether a criterion associated with a tear film quality of the subject's eye is not satisfied, which comprises:
       the optical measurement instrument detecting the tear film quality of the subject's eye;
       the optical measurement instrument determining when the tear film quality of the subject's eye meets a specified quality threshold; and
       when the tear film quality of the subject's eye does not meet the specified quality threshold, determining that the criterion is not satisfied; and
    in response to determining that the criterion is not satisfied, taking one or more corrective actions to measure the characteristic of the subject's eye under a condition wherein the criterion is satisfied.

11. The method of claim 10, wherein detecting the tear film quality of the subject's eye comprises detecting at least one of the thinness of the tear film and a breakup of the tear film.

12. A method for measuring a characteristic of a subject's eye, the method comprising:
    an optical measurement instrument receiving from an operator, via a user interface of the optical measurement instrument, a begin measurement instruction indicating the start of a measurement period for objectively measuring at least one characteristic of the subject's eye;
    subsequent to receiving the begin measurement instruction, determining whether a criterion associated with the tear film quality of the subject's eye is not satisfied; and
    in response to determining that the criterion is not satisfied, taking one or more corrective actions to measure the characteristic of the subject's eye under a condition wherein the criterion is satisfied, which comprises at least one of:

providing an indication to the operator via the user interface that the subject should blink; and the optical measurement instrument objectively measuring the at least one characteristic of the subject's eye only at times when the tear film quality of the subject's eye meets the specified quality threshold.

13. A method for measuring a characteristic of a subject's eye, the method comprising:

an optical measurement instrument receiving from an operator, via a user interface of the optical measurement instrument, a begin measurement instruction indicating the start of a measurement period for objectively measuring at least one characteristic of the subject's eye;

subsequent to receiving the begin measurement instruction, determining whether a criterion associated with the tear film quality of the subject's eye is not satisfied, which comprises determining whether the subject's eye exhibits excessive tearing; and in response to determining that the criterion is not satisfied, taking one or more corrective actions to measure the characteristic of the subject's eye under a condition wherein the criterion is satisfied, which comprises, in response to determining that the subject's eye exhibits excessive tearing, causing objective measurement of the at least one characteristic of the subject's eye to be delayed by a specified delay.

14. An optical measurement instrument, comprising:

an optical system configured for objectively measuring at least one characteristic of a subject's eye;

a user interface; and one or more processors, the one or more processors being configured to receive via the user interface a begin measurement instruction indicating the start of a measurement period for objectively measuring at least one characteristic of the subject's eye, subsequent to receiving the begin measurement instruction to determine whether a criterion associated with the tear film quality of the subject's eye is satisfied, and in response to determining that the criterion is not satisfied, to take one or more corrective actions to measure the characteristic of the subject's eye under a condition where the criterion is satisfied, wherein the one or more processors are further configured to:

determine whether an elapsed time period associated with the subject blinking exceeds a threshold; and in response to determining that the elapsed time period associated with the subject blinking exceeds the threshold, provide an indication via the user interface to the operator that the subject should blink.

15. The optical measurement instrument of claim 14, wherein the one or more processors are further configured to measure a time interval from a last time when the subject last blinked.

16. The optical measurement instrument of claim 15, further comprising a blink detection camera configured to capture a series of images of the subject's eye, and wherein the one or more processors are further configured to:

detect from the captured images a blink of the subject's eye; and in response to detecting a blink of the subject's eye, reset the time interval.

17. The optical measurement instrument of claim 16, wherein the blink detection camera is an eye alignment camera.

18. The optical measurement instrument of claim 15, further comprising an eye alignment camera separate from a blink detection camera.

19. The optical measurement instrument of claim 14, wherein the one or more processors are further configured to measure the elapsed time period from a start time corresponding to a time when the begin measurement instruction is received by the optical measurement instrument.

20. The optical measurement instrument of claim 19, wherein the one or more processors are further configured to receive from the operator via the user interface another begin measurement instruction in response to the indication via the user interface to the operator that the subject should blink.

21. The optical measurement instrument of claim 14, wherein the user interface comprises a display, and wherein the indication to the operator that the subject should blink comprises a progress bar displayed on the display, the progress bar being reset to zero when the subject blinks.

22. The optical measurement instrument of claim 21, wherein the progress bar changes color to indicate when the elapsed time period exceeds the threshold.

23. An optical measurement instrument, comprising:

an optical system configured for objectively measuring at least one characteristic of a subject's eye;

a user interface; and one or more processors, the one or more processors being configured to receive via the user interface a begin measurement instruction indicating the start of a measurement period for objectively measuring at least one characteristic of the subject's eye, subsequent to receiving the begin measurement instruction to determine whether a criterion associated with the tear film quality of the subject's eye is satisfied, and in response to determining that the criterion is not satisfied, to take one or more corrective actions to measure the characteristic of the subject's eye under a condition where the criterion is satisfied, wherein the optical measurement instrument is configured to:

detect the tear film quality of the subject's eye;

determine when the tear film quality of the subject's eye meets a specified quality threshold; and when the tear film quality of the subject's eye does not meet the specified quality threshold, determine that the criterion is not satisfied.

24. The optical measurement instrument of claim 23, wherein the optical measurement instrument is configured to detect at least one of a thinness of the tear film and a breakup of the tear film.

25. An optical measurement instrument, comprising:

an optical system configured for objectively measuring at least one characteristic of a subject's eye;

a user interface; and one or more processors, the one or more processors being configured to receive via the user interface a begin measurement instruction indicating the start of a measurement period for objectively measuring at least one characteristic of the subject's eye, subsequent to receiving the begin measurement instruction to determine whether a criterion associated with the tear film quality of the subject's eye is satisfied, and in response to determining that the criterion is not satisfied, to take one or more corrective actions to measure the characteristic of the subject's eye under a condition where the criterion is satisfied, wherein to take one or more corrective actions comprises at least one of:

the one or more processors are further configured to provide an indication to the operator via the user interface that the subject should blink; and the optical measurement instrument is configured to objectively measure the at least one characteristic of the subject's eye only at times when the tear film quality of the subject's eye meets the specified quality threshold.

26. An optical measurement instrument, comprising:

an optical system configured for objectively measuring at least one characteristic of a subject's eye;

a user interface; and one or more processors, the one or more processors being configured to receive via the user interface a begin measurement instruction indicating the start of a measurement period for objectively measuring at least one characteristic of the subject's eye, subsequent to receiving the begin measurement instruction to determine whether a criterion associated with the tear film quality of the subject's eye is satisfied, and in response to determining that the criterion is not satisfied, to take one or more corrective actions to measure the characteristic of the subject's eye under a condition where the criterion is satisfied, wherein the optical measurement instrument is configured to determine whether the subject's eye exhibits excessive tearing; and in response to determining that the subject's eye exhibits excessive tearing, to cause objective measurement of the at least one characteristic of the subject's eye to be delayed by a specified delay.

* * * * *